United States Patent
de Vries

(10) Patent No.: US 7,590,448 B2
(45) Date of Patent: Sep. 15, 2009

(54) METHOD AND APPARATUS FOR PREVENTION OF ATRIAL TACHYARRHYTHMIAS

(75) Inventor: Bernhard de Vries, Dieren (NL)

(73) Assignee: Medtronic, Inc., Minneapolis, MN (US)

( * ) Notice: Subject to any disclaimer, the term of this patent is extended or adjusted under 35 U.S.C. 154(b) by 451 days.

(21) Appl. No.: 11/380,246

(22) Filed: Apr. 26, 2006

(65) Prior Publication Data
US 2007/0255325 A1  Nov. 1, 2007

(51) Int. Cl.
*A61N 1/362* (2006.01)
(52) U.S. Cl. ............................................. 607/14; 607/9
(58) Field of Classification Search ............... 607/9, 607/14; 600/16
See application file for complete search history.

(56) References Cited

U.S. PATENT DOCUMENTS

| | | | |
|---|---|---|---|
| 5,403,356 A | 4/1995 | Hill et al. | |
| 5,658,320 A | 8/1997 | Betzold et al. | |
| 5,968,079 A | 10/1999 | Warman et al. | |
| 5,991,657 A | 11/1999 | Kim | |
| 6,052,620 A | 4/2000 | Gillberg et al. | |
| 6,185,459 B1 | 2/2001 | Mehra et al. | |
| 6,442,427 B1 | 8/2002 | Boute et al. | |
| 6,508,771 B1 * | 1/2003 | Padmanabhan et al. | 600/515 |
| 6,895,272 B2 | 5/2005 | Siem et al. | |

FOREIGN PATENT DOCUMENTS

WO WO2005105205 A 11/2005

OTHER PUBLICATIONS

"Multisite Pacing for AF management—Technical and Clinical Challenges"; Mehra, et al., Journal of Interventional Cardiac Electrophysiology, 2000; 4:69-79.

* cited by examiner

*Primary Examiner*—Carl H Layno
*Assistant Examiner*—Brian T Gedeon
(74) *Attorney, Agent, or Firm*—Michael C. Soldner; Scott A. Bardell

(57) ABSTRACT

A multi-site atrial pacemaker capable of delivering pacing pulses to one location synchronized to sensed or paced atrial depolarizations on another location and a method of its use. A defined interval is defined following atrial depolarizations during which such synchronized atrial pacing pulses may not be delivered. The pacemaker automatically adjusts the duration of the defined interval to produce a minimum level of induced tachyarrhythmias. Generally, this desired result is accomplished by measuring coupling intervals of PACs, monitoring occurrences of atrial tachyarrhythmias associated with PACs and adjusting the defined interval accordingly.

12 Claims, 6 Drawing Sheets

METHOD AND APPARATUS FOR PREVENTION OF ATRIAL TACHYARRHYTHMIAS

FIELD OF THE INVENTION

The present invention relates generally to the field of implantable stimulators and more particularly to cardiac pacemakers and implantable antiarrhythmia devices.

BACKGROUND OF THE INVENTION

Multi-site atrial pacing, for example bi-atrial pacing, is a known method of reducing the incidence of atrial tachyarrhythmias. In this pacing mode, atrial pacing electrodes are located at two sites within the atria. In response to sensing an atrial depolarization at one site, pacing pulses are delivered either to both sites or to the site at which the depolarization was not sensed. In the context of this pacing mode, the issue of whether to provide a pacing pulse or pulses in response to a sensed atrial premature depolarization, also referred to as a premature atrial contraction (PAC) has arisen, as in some cases pacing pulses synchronized to PACs can be pro-arrhythmic.

The issue of the possible pro-arrhythmic effect of PAC synchronized atrial pacing pulses is dealt with in the article "Multisite Pacing for AF management—Technical and Clinical Challenges"; Mehra, et al., Journal of Interventional Cardiac Electrophysiology, 2000; 4:69-79, incorporated in its entirety by reference herein. In this article, it is proposed that pacing pulses should not be delivered synchronized to PACs occurring at short coupling intervals from previous atrial depolarizations, but should be delivered synchronized to PACs having longer coupling intervals. An exemplary pacemaker for accomplishing this result is disclosed in U.S. Pat. No. 5,403,356, issued to Hill, et al., also incorporated herein by reference in its entirety. In this patent, a defined "APB interval" following an atrial depolarization is defined by the pacemaker. Non-refractory sensed PACs within this interval do not trigger synchronized pacing pulses. PACs sensed outside this interval do. In the particular embodiment disclosed in this patent, the duration of the APB interval varies as a result of sensed atrial rate. Automatic adjustment of anti-arrhythmia pacing modes and parameters generally is disclosed in U.S. Pat. No. 6,185,459, issued to Mehra, et al., also incorporated herein by reference in its entirety.

SUMMARY OF THE INVENTION

The present invention is directed to a method and apparatus for automatically adjusting the duration of an APB interval as in the Hill, et al. patent, to produce a minimum level of induced tachyarrhythmias. Generally, this desired result is accomplished by monitoring occurrences of atrial tachyarrhythmias following PACs and adjusting the APB interval accordingly. PACs are identified as being within a defined interval following a preceding sensed atrial depolarization or delivered atrial pacing pulse. Atrial tachyarrhythmia detection may be accomplished using any of the various known mechanisms.

In some embodiments, if an atrial tachyarrhythmia occurs following a PAC having an associated synchronized pacing pulse, the duration of the APB interval may be increased to extend past the coupling interval of the sensed PAC. Conversely, if an atrial tachyarrhythmia occurs following a sensed PAC without synchronized pacing, the APB interval may be reduced so that the coupling Interval of the sensed PAC is outside the APB interval. In some embodiments, adjustment of the APB interval may occur following a single occurrence of an atrial tachyarrhythmia following a PAC. In other embodiments, adjustment of the APB interval may require multiple occurrences of atrial tachyarrhythmia's occurring in the presence of PACs at or about a specific coupling interval. In some embodiments, the numbers of sensed tachyarrhythmias at different PAC coupling intervals may be stored in the form of a histogram to facilitate this analysis.

The invention may be practiced in a pacemaker as in the Hill, et al. patent, in which the APB interval is varied as a function of atrial rate or in pacemakers in which the APB interval is not rate-variable. Further, while the invention is disclosed herein in its simplest form, i.e. a bi-atrial pacer, the invention may also be incorporated into multi-site atrial pacemakers with ventricular sensing and pacing functions similar to those disclosed in the cited Mehra, et al. patent. The invention of course may also be incorporated into devices such as anti-arrhythmia pacemakers and implantable cardioverter-defibrillators, which have the capability of treating detected tachyarrhythmias.

Finally, while the invention is disclosed in the context of a bi-atrial pacemaker, it is also believed useful in the context of other multi-site atrial pacemakers. For example, the invention may be practiced in pacemakers in which electrodes are located in the right atrial appendage and Triangle of Koch, as disclosed in the cited Hill, et al. patent or in which synchronized atrial pacing occurs at more than two sites.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

Figure 1:
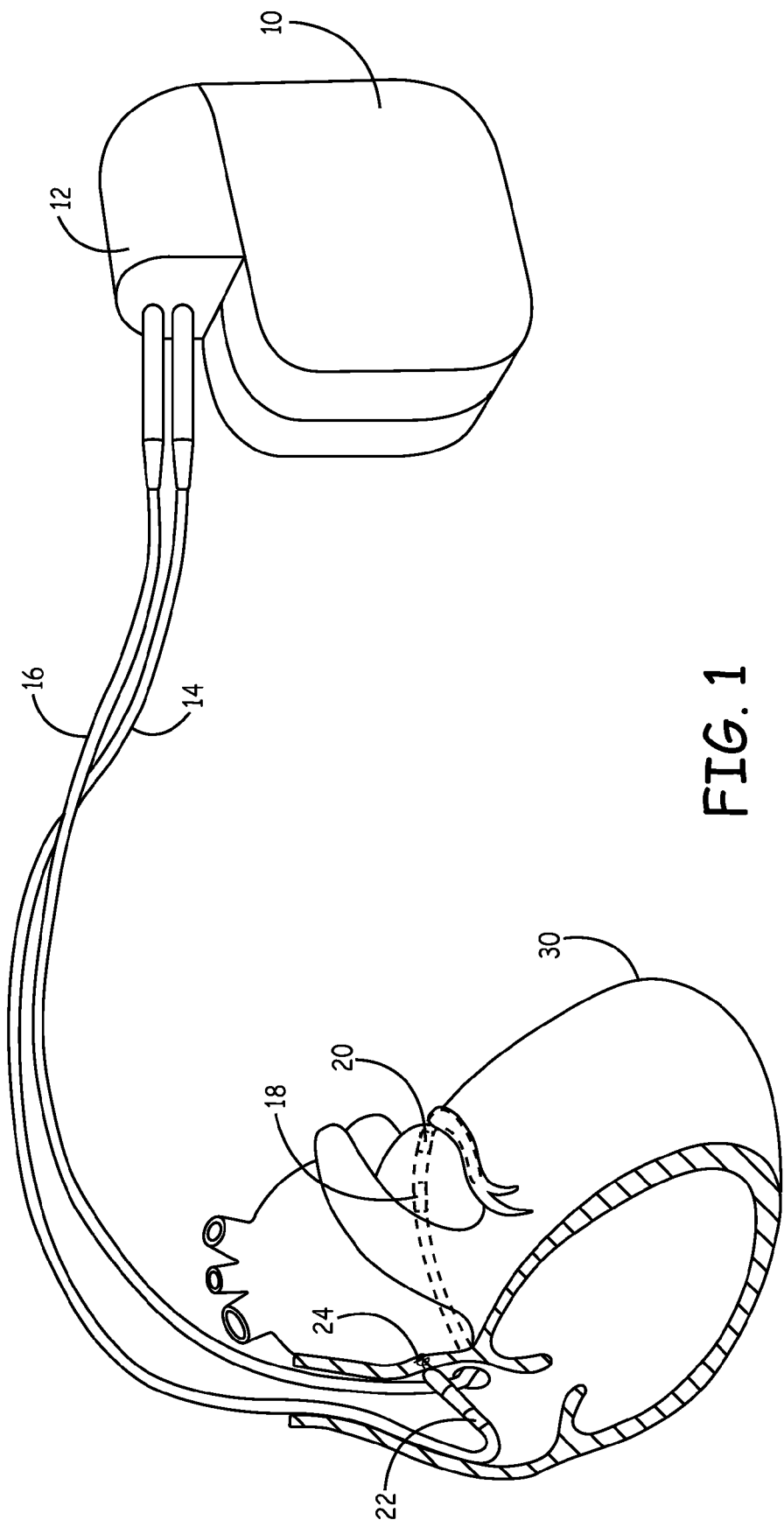
FIG. 1 is a drawing illustrating the interconnection of a cardiac pacemaker according to the present invention with the right and left atria of a human heart.

In the drawings described below, identically numbered components in the various drawings should be understood to be identical structures or steps.

FIG. 1 shows an implantable pacemaker 10, according to the present invention, and its interconnection to a human heart 30. The pacemaker is provided with two leads 14 and 16, coupled to the pacemaker by means of a connector block 12.

Leads 14 and 16 take the form of bipolar endocardial leads, of the type presently available and widely marketed for use in conjunction with cardiac pacemakers. These leads are provided with proximal electrodes (18, 22) and distal electrodes (20, 24). The electrode 24 adjacent the distal end of lead 14 is a helical electrode screwed into the tissue of the right atrium. Pacing and sensing using this lead is accomplished using ring electrode 22 and electrode 24. Lead 16 is located in the coronary sinus and is similarly employed to sense and pace the left atrium using electrodes 18 and 20. Other electrode locations within or adjacent to the atria may also be employed in conjunction with the present invention. For example, electrodes located in the triangle of Koch may be employed in conjunction with electrodes located in an area displaying prolonged refractory periods. Alternatively, electrodes located in an area displaying prolonged refractory periods may be employed in conjunction with electrodes located elsewhere in the right atrium. Alternatively, three or more electrode locations in or adjacent the right and/or left atria may be employed.

Figure 2:
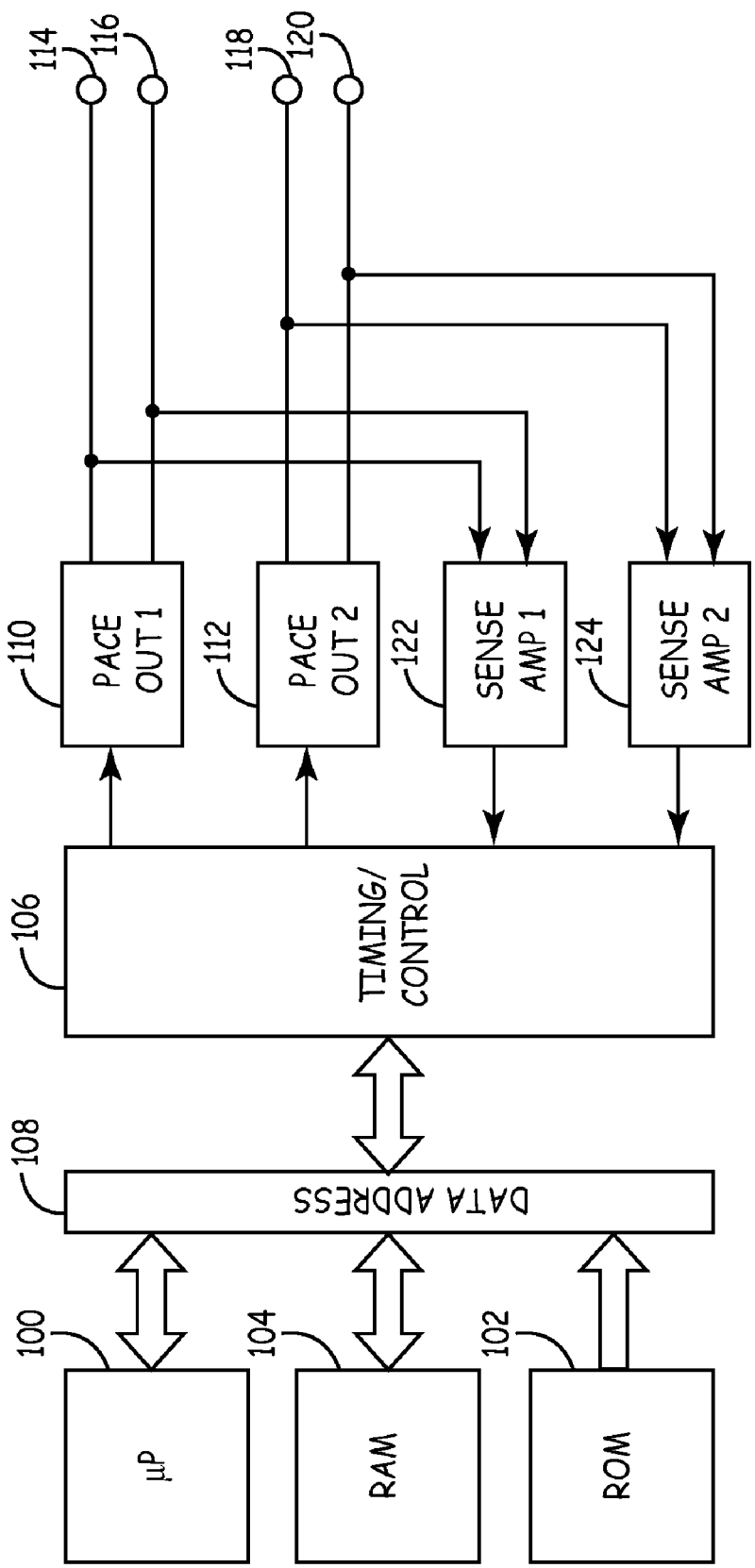
FIG. 2 is a block functional diagram of a cardiac pacemaker appropriate for use in practicing the present invention.

FIG. 2 is a block, functional diagram of a pacemaker appropriate for use in conjunction with the present invention. Because the diagram as illustrated makes use of presently available components and circuitry, only the basic functional operation as it relates to the present invention is described in detail. As a practical matter, it is believed that any of the available microprocessor controlled dual chamber (DDD, VDD) pacemakers presently on the market can readily be modified to practice the present invention, as they typically include all of the basic functional components illustrated.

In the embodiment illustrated, operation of the pacemaker is controlled by the microprocessor 100, under control of programming stored in read only memory (ROM) 102. Random access memory (RAM) 104 serves to store those parameters which are programmable by the physician, to store measurements made by the pacemaker and values calculated by the microprocessor. The RAM 104 may also be employed to store electrograms sensed by the pacemaker.

Microprocessor 100 is coupled to timing and control circuitry 106 by means of a data/address bus 108. Timing and control circuitry 106 takes the form of a number of counters or timers for defining the time intervals discussed below in conjunction with FIG. 3. The time intervals provided are intended to be programmable and to be varied under control of microprocessor 100.

Pulse generator 110 is coupled to electrodes 114 and 116, which may correspond to the electrodes located on lead 14, in FIG. 1. In particular, electrode 114 may correspond to ring electrode 22, and electrode 116 may correspond to the helical electrode 24. Pulse generator circuitry 112 is coupled to electrodes 118 and 120, which may correspond to the electrodes on lead 16 (FIG. 1). In particular, electrode 118 may correspond to ring electrode 18, and electrode 120 may correspond to electrode 20 in FIG. 1. Sense amp 122 is coupled to electrodes 114 and 116. Sense amp 124 is coupled to electrodes 118 and 120.

Timing/control circuitry 106, in the context of the present invention, defines a number of basic timing intervals. The first timing interval is the escape interval, corresponding to basic pacing rate of the device, as is conventional in cardiac pacemakers. In response to time-out of the escape interval, timing/control circuitry 106 triggers pulse generators 110 and 112 to deliver cardiac pacing pulses. Time out of the escape interval also serves as an interrupt, triggering microprocessor 100 to perform any necessary calculations or updating and to reset the timers within timing/control circuitry 106.

Also defined by timing/control circuit 106 are blanking and refractory periods, corresponding functionally to blanking and refractory periods in traditional cardiac pacemakers and applicable to both sense amps 122 and 124. During the blanking period, sense amps 122 and 124 are disabled. During the portion of the refractory period extending beyond the blanking period, sense amps 122 and 124 are enabled. However, atrial depolarizations sensed by either sense amp during this period will not function to reset the basic rate interval. During the refractory period, sensing for noise or other interference may also be conducted, as currently done in conjunction with presently available cardiac pacemakers. In the event that a delay is provided between the sensing of depolarizations and delivery of pacing pulses, the control/timing circuitry would function to time this delay as well.

Timing/control circuitry 106 also defines the APB interval discussed above. In some embodiments, the APB interval may vary as a function of the measured atrial rate, over a preceding series of beats. For example, APB may be a defined percentage (e.g. one-half) of the average interval separating atrial depolarizations, over a preceding series of 8 beats. In such embodiments, this percentage may be adjusted as a function of the occurrences of tachyarrhythmias following PACs, as discussed in more detail below.

In response to an atrial depolarization sensed by amplifier 122, following the APB interval, timing/control circuitry 106 may trigger only pulse generator 112 to deliver a pacing pulse or may trigger both pulse generators 110 and 112 to deliver pacing pulses. Similarly, in response to an atrial depolarization sensed by amplifier 124, outside the APB interval, timing/control circuitry 106 may trigger only pulse generator 110 to deliver a pacing pulse or may trigger both pulse generators 110 and 112 to deliver pacing pulses. Microprocessor 100 is interrupted, and the escape interval, blanking interval, refractory interval and APB intervals timed by control/timing circuitry 106 are reset. The A-A interval is stored for later reference. A-A intervals which are less than a defined duration are flagged by the microprocessor as PAC coupling intervals and are employed to update the APB interval responsive to occurrences of atrial tachyarrhythmias as discussed below.

In embodiments employing a rate variable APB interval, microprocessor 100 may also update a running average of the preceding series of A-A intervals between sensed and paced atrial depolarizations, based on the time of occurrence of the most recent depolarization. Microprocessor 100 may then recalculate a new APB interval, based on the updated average. In response to a depolarization sensed by amplifier 122, within the APB period, microprocessor 100 is interrupted, and the escape interval, blanking interval, refractory interval and APB intervals timed by control/timing circuitry 106 are reset. The A-A interval (PAC coupling interval) is stored for later reference. Timing/control circuitry 106 does not trigger pulse generator 112 to deliver a pacing pulse or pulses. In those embodiments employing rate-variable APB intervals the A-A interval ending in the premature atrial beat is not employed to update the running average of the A-A intervals.

In the event that the escape interval times out, pacing pulses are delivered by output circuits 110 and 112, microprocessor 100 is interrupted and the escape interval, blanking interval, refractory interval and APB intervals timed by control/timing circuitry 106 are reset. In those embodiments employing rate-variable APB intervals the escape interval is used to update the average A-A interval, purposes of calculating a new value of the APB interval.

In the context of the present invention, the microprocessor 100 is also employed to analyze the occurrences and timing of atrial depolarizations to detect occurrences of tachyarrhythmias, especially atrial tachyarrhythmias. This analysis may be as simple as detection of an excessively high rate, or may employ measurements of other factors such a rate stability, suddenness of rapid rate onset depolarization waveform morphology or the like. Any known method of tachyarrhythmia detection may be employed, as the invention does not depend on any particular mechanism for tachyarrhythmia detection. Exemplary mechanisms for tachyarrhythmia detection may be found in U.S. Pat. No. 5,658,320 issued to Betzold et al., U.S. Pat. No. 5,968,079 issued to Warman, et al., U.S. Pat. No. 5,991,657 issued to Kim, U.S. Pat. No. 6,895,272 issued to Siem et al. and U.S. Pat. No. 6,052,620 issued to Gillberg et al, all incorporated herein by reference in their entireties. The particular detection methodology chosen will of course depend on the configuration of the pacemaker, e.g. whether it includes ventricular sensing capabilities.

In response to detection of an atrial tachyarrhythmia, the microprocessor 100 preferably determines whether the tachyarrhythmia is associated with a preceding PAC. This may be accomplished by determining whether a PAC occurred within a defined number of beats or a defined time interval prior to onset of the detected tachyarrhythmia. If so, the PAC's coupling interval is stored as part of a histogram. The histogram includes a number of defined bins, each of which extends over a range of PAC coupling intervals and stores a number indicating the number of occurrences of measured PAC coupling intervals occurring within the range defined by the bin. The histogram may extend over a defined number of preceding stored PACs, over a defined duration, or may simply continue to be updated until reset. The microprocessor 100 examines the histogram to determine whether any of the bins holds a value which meets a threshold number, indicating that PAC coupling intervals in this range are associated with occurrences of tachyarrhythmias. If the threshold is reached, the microprocessor adjusts the APB interval accordingly. This procedure is discussed in more detail in conjunction with FIGS. 4-6.

Figure 3:
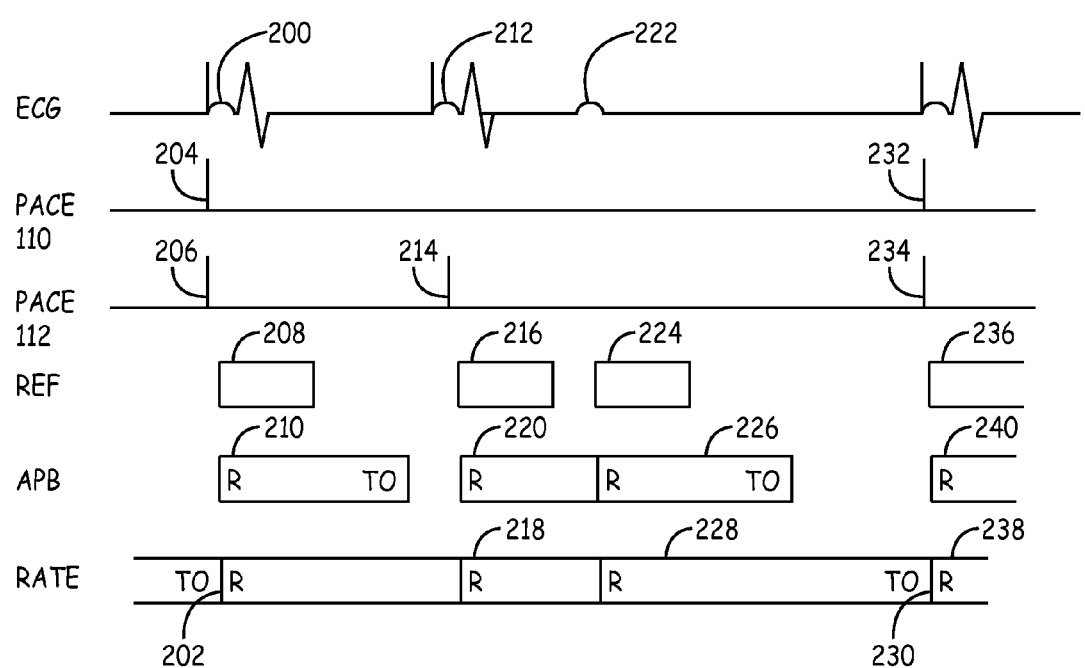
FIG. 3 is a simulated electrogram tracing in conjunction with a timing chart, indicating the operation of the various time intervals defined by a pacemaker according to a preferred embodiment of the invention.

FIG. 3 illustrates a simulated electrocardiogram (ECG) and associated timing charts, showing the interrelation of the various time intervals defined by the apparatus of FIG. 2. The simulated ECG begins with a paced atrial depolarization at 200. This event occurs as the result of a time out of the base pacing rate interval at 202, triggering pacing pulses delivered by both pulse generators (PACE 110 and PACE 112) at 204 and 206, respectively. Also illustrated are the refractory interval 208, initiated in responses to delivery of pacing pulses at 204 and 206 and the APB interval 210, similarly initiated following delivery of pacing pulses. APB interval 210 is updated by the microprocessor, following delivery of the pacing pulses, and extends for a predetermined period corresponding to a proportion or fraction of the current average atrial rate.

At 212, a spontaneous atrial depolarization is sensed by sense amp 122. Because depolarization 212 follows the expiration of APB interval 210, a pacing pulse 214 is delivered by pulse generator 112. Alternatively, pacing pulses may be delivered by both pulse generators, as discussed above. The refractory interval 216 and escape interval 218 are restarted. In embodiments employing rate variable APB intervals, the APB interval 220 is updated by the microprocessor and correspondingly restarted. At 222, a premature atrial beat occurs, coming before time-out of APB interval 220. In response to the atrial premature beat 222, the refractory period 224, APB period 226 and escape interval 228 are all restarted. However, in embodiments employing rate variable APB intervals, APB interval 226 is not updated to take into account the interval between depolarizations 212 and 222.

At 230, the basic rate interval times out, triggering delivery of pacing pulses 232 and 234, by both pulse generators. The refractory interval 236 and the escape interval 238 are both restarted. In embodiments employing rate variable APB intervals, APB interval 240 is updated to reflect the A-A interval (the escape interval) between spontaneous depolarization 222 and delivery of the cardiac pacing pulses at 232, 234.

Figure 4:
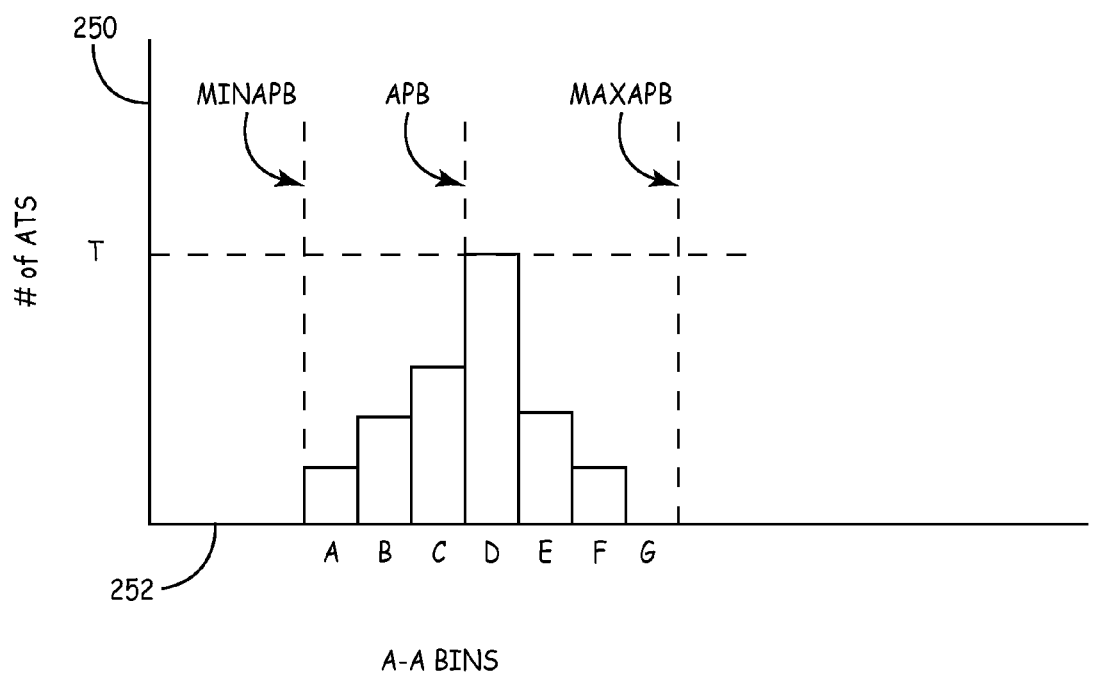
FIG. 4 is an exemplary histogram illustrating one method of storing and organizing information related to occurrences of tachyarrhythmias occurring at different PAC coupling intervals

FIG. 4 is an exemplary histogram of a type that may be employed in conjunction with the present invention. The histogram defines a number of bins A-G, extending along a time axis 252. Preferably the bins define time interval ranges extending between a minimum available APB interval duration (MINAPB) and a maximum available APB interval duration (MAXAPB). Depending on the specific implementation of the device, the bins may either be of defined duration range or a defined percentage of the range between APBMIN and APBMAX. A defined numerical threshold T is indicated along a vertical numeric axis 250. In the simplest embodiment, the value of T could be set equal to one, resulting in adjustment of the APB interval following a single detected tachyarrhythmia. Alternatively, the value of T is set by the physician as indicative of an undesirable number of occurrences of tachyarrhythmias over the time duration or number of intervals reflected in the histogram, with the hope that frequency of tachyarrhythmias can ultimately be reduced below this level by appropriate adjustment of the APB. The counts of PAC coupling intervals in each bin are illustrated by means of the associated vertically extending bar.

As illustrated, the duration of the APB interval is preferably located at the lower or upper interval duration for one of the bins. In embodiments employing rate variable APB intervals, the bins may need to be adjusted following rate-based adjustment of the APB as discussed hereinbelow (e.g. bin ranges adjusted upward or downward) in order to maintain this relationship. In response to detection of an atrial tachyarrhythmia, the microprocessor 100 checks to determine whether any bin has a count that meets the threshold. If so, the duration of the APB interval is adjusted. If the bin meeting the threshold extends over intervals less than the duration of the APB interval, this indicates that PACs occurring in that interval range were not accompanied by synchronized pacing. The duration of the APB interval may then be set equal to the lower duration of the bin meeting the threshold to assure that subsequent PACs in this interval range are accompanied by synchronized pacing. If the bin meeting the threshold contains intervals greater than the APB interval, this indicates that the PACs in that interval range were accompanied by synchronized pacing. The duration of the APB interval may then be set equal to the lower duration of the bin meeting the threshold to assure that subsequent PACs in this interval range are not accompanied by synchronized pacing. Following adjustment of the APB interval based on occurrences of atrial tachyarrhythmias, the histogram is preferably cleared or reset.

In an even simpler embodiment, the histogram could be dispensed with entirely. The APB interval could be reset following an atrial tachyarrhythmia associated with a PAC by simply adjusting the APB interval to be greater than the coupling interval of the PAC if synchronized pacing was delivered and adjusting the APB interval to be less than the coupling interval of the PAC if synchronized pacing was not delivered.

Figure 5:
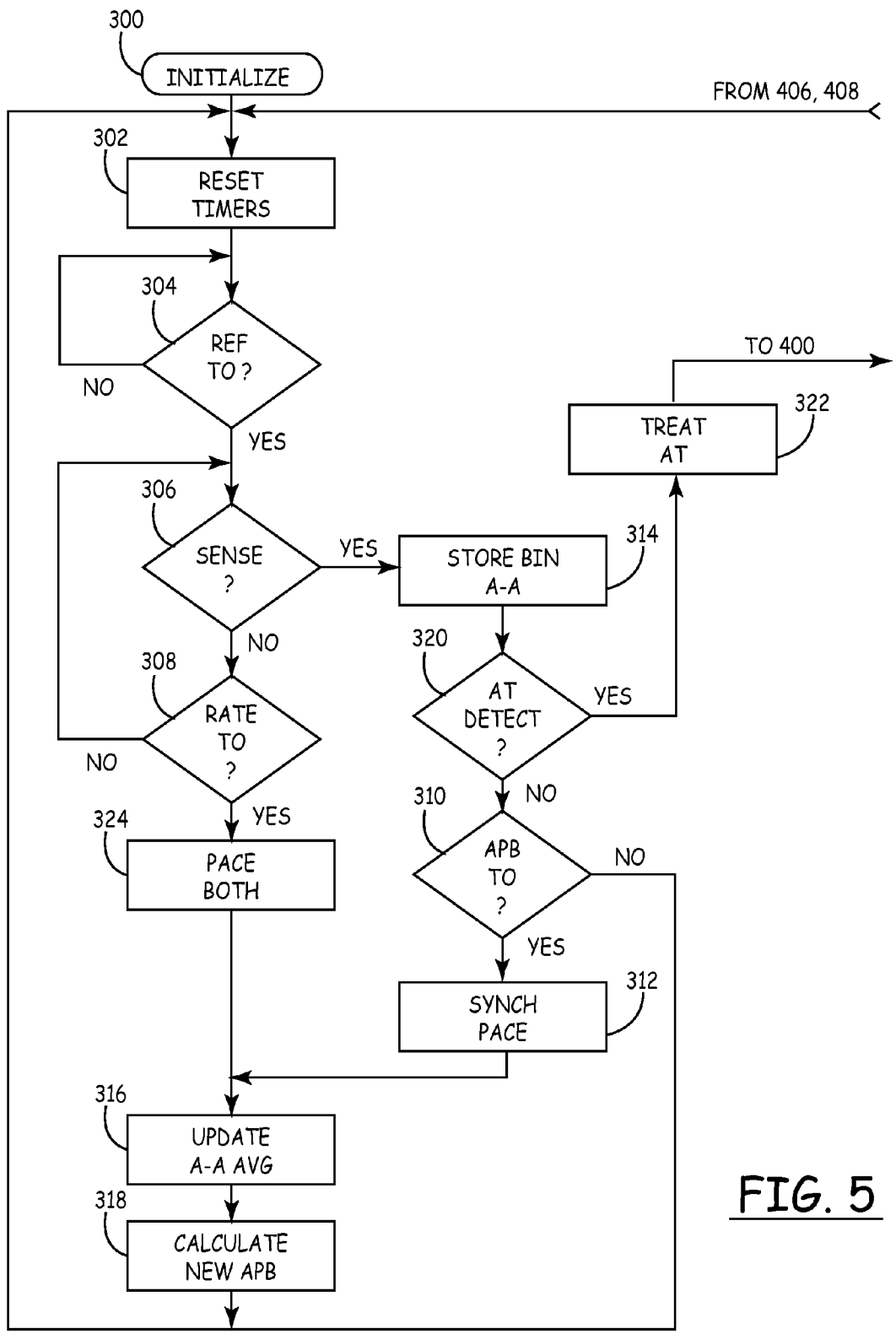
FIG. 5 is a functional flowchart, illustrating the basic operation of a pacemaker according to a preferred embodiment of the invention.

FIG. 5 is a functional flow chart illustrating the operation of the device of FIG. 2, as it practices the present invention. At 300, the device is initialized. This may correspond to initial hook-up of the device to the battery, or to reprogramming of the device by physician. At 302 the microprocessor is awakened, resetting the time intervals in the control/timing circuitry, including the blanking interval, refractory interval, APB interval and escape interval. At 304 the device waits until the refractory interval has timed out.

When the refractory interval has timed out, the device awaits the occurrence of an atrial sense event at 306 or time out of the escape interval at 308. If an atrial depolarization is sensed by either sense amp, the A-A interval is measured and stored. If its duration is short enough to qualify as a PAC, for example if it falls within the interval ranges defined in the stored histogram (FIG. 4), the A-A interval (PAC coupling interval) is binned in the histogram at 314. The microprocessor within the device checks at 320 to determine whether a tachyarrhythmia is present. If not, the device checks at 310 to determine whether the APB interval has timed out. This may be accomplished by the microprocessor, or by fixed logic within the timing/control circuitry.

If the APB interval has not timed out at the time the atrial depolarization is sensed, the device is simply reset at 302, and the average A-A interval and APB intervals remain unchanged. If the APB interval has timed out when the atrial depolarization is sensed, at 112 the device delivers synchronized pacing pulses at one or both pairs of atrial electrodes as discussed above. The synchronized pacing pulse or pulses may be delivered essentially simultaneously with the detection of the atrial depolarization, or may be delivered following a short delay period, e.g. less than 50 ms.

If the device employs a rate variable APB, the A-A average is updated at 316 and a new APB value is calculated at 318, as described in the cited Mehra et al. patent. The bin ranges of the histogram are also preferably adjusted upward or downward to retain the alignment of the APB interval with the end value of its associated bin value. If a rate variable APB interval is not employed, following delivery of synchronized pacing at 312, the device simply returns to reset the timers at 302.

In the event that no atrial depolarizations are sensed prior to timeout of the basic rate interval, as indicated at 308, both pulse generators are activated at 324. If the device employs a rate variable APB, The microprocessor updates the A-A average using the escape intervals the measured A-A interval, calculates a new APB interval at 318, and the device is reset at 302. Otherwise the device simply resets the timers at 302.

In the event that an atrial tachyarrhythmia is detected at 320, in embodiments in which antitachycardia therapies are available, they are delivered at 322. While delivery of such therapies is not necessary for the present invention, it is anticipated that the invention may be practiced in devices capable of such therapy delivery. For example, devices as described in the above-cite Gillberg et al. patent. After detection at 320 or therapy delivery at 322, the device determines whether the APB interval needs to be adjusted, as illustrated in FIG. 6.

Figure 6:
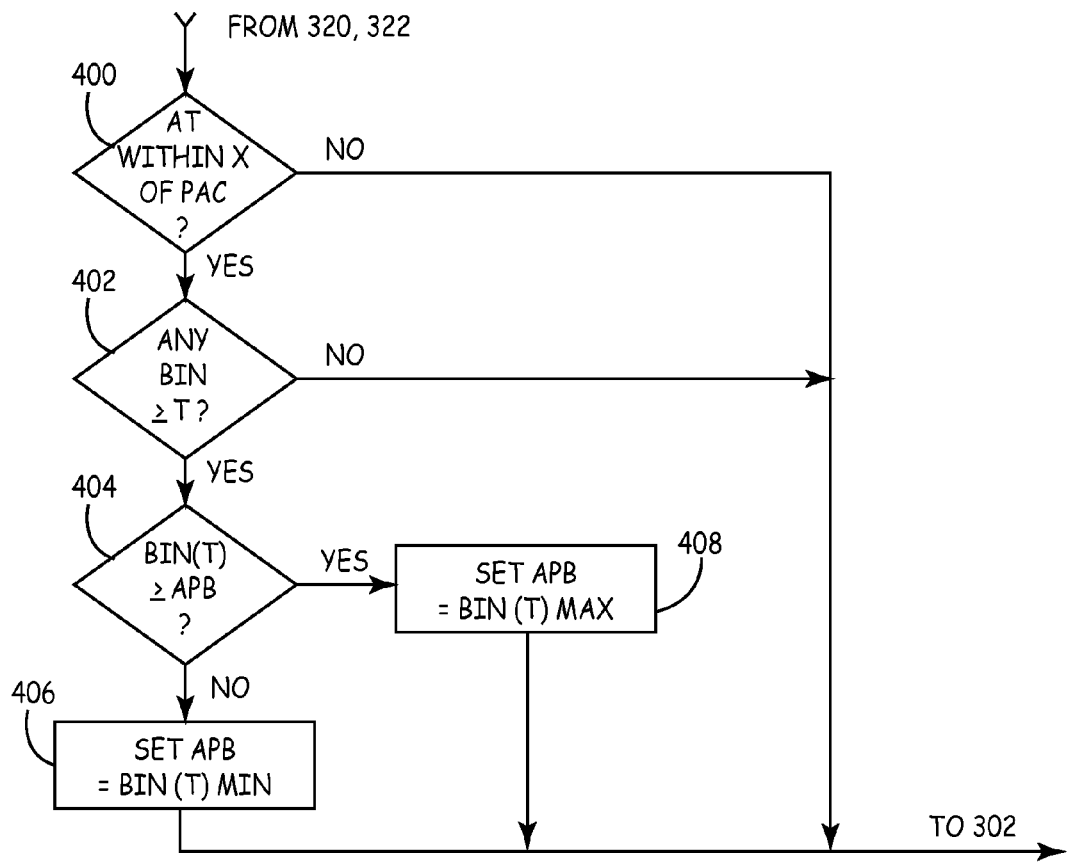
FIG. 6 is a functional flow chart generally illustrating adjustment of the APB interval according to a preferred embodiment of the present invention.

FIG. 6 is a functional flow chart illustrating the operation of the device to adjust the APB interval responsive to occurrence of atrial tacharrhythmias. Following detection of a tachyarrhythmia at 320 (FIG. 5), the microprocessor within the device checks at 400 to determine whether the detected tachyarrhythmia was associated with a preceding PAC. For example, this may be accomplished by determining whether a preceding PAC occurred within a defined time period or number of beats preceding onset of the tachyarrhythmia. If not, the device may simply return to reset the timers at 302 (FIG. 5.) If a PAC is associated with the detected tachyarrhythmia, the device checks at 402 to determine whether the count in any of the histogram bins meets the defined threshold value. If not, the device may simply return to reset the timers at 302 (FIG. 5.)

If the count in a particular bin "BIN(T)" meets the threshold the device checks at 404 to determine whether the bin includes interval durations greater than the duration of the APB. If so, as discussed above in conjunction with FIG. 4, the duration of APB is set equal to the maximum duration of BIN(T) at 408. Otherwise, the duration of APB is set equal to the minimum duration of BIN(T) at 406.

The basic operation of pacemakers according to the present invention can readily be extended to apply to systems employing three or more electrode locations. In response to a sensed depolarization at any of the electrodes, pacing pulses may be applied to all electrodes or only to the electrodes other than those through which the depolarization was sensed.

While the embodiment disclosed above employs separate sense amps and pulse generators for each electrode pair, It is believed within the scope of the present invention to employ fewer sense amps and pulse generators, so long as the required functions are present. For example, a single pulse generator could supply all electrodes with pacing pulse, with switching circuits to direct pulses to the desired electrodes or electrode pairs. Similarly, by switching, time multiplexing or other means, one sense amp could be shared by two or more electrodes or electrode pairs.

Further, while it is believed that for practical purposes, commercial implementations of devices employing the present invention will generally take the form of microprocessor controlled pacemakers, the invention and its associated functions may also readily be practiced by means of a pacemaker based on full custom digital integrated circuitry as widely practiced in the pacing industry, or may even be practiced in the form of a device fabricated of commercially available discrete components and circuits, so long as basic functions set forth above are preserved. Therefore, the disclosed embodiments should be considered exemplary, rather than limiting with regard to the claims that follow.

The invention claimed is:

1. A pacemaker, comprising;
first and second atrial electrodes;
an atrial sense amplifier responsive to atrial depolarizations and coupled to the first atrial electrode;
an atrial pacing pulse generator coupled to the second atrial electrode;
control circuitry coupled to the atrial sense amplifier and to the pulse generator, defining first time intervals extending for a defined duration following atrial depolarizations and triggering generation of pacing pulses by the pulse generator synchronized only to subsequent atrial depolarizations sensed by the atrial sense amplifier outside the first time intervals, the control circuitry further comprising an atrial tachyarrhythmia detector and means for adjusting the duration of the first time intervals responsive to detections of atrial tachyarrhythmias.

2. A pacemaker according to claim 1, wherein the adjusting means comprises means responsive to the atrial sense amplifier for identifying occurrences of Premature Atrial Contractions (PACs) and for measuring coupling intervals separating them from preceding atrial depolarizations.

3. A pacemaker according to claim 2 wherein the adjusting means increases the duration of the first time intervals responsive to tachyarrhythmias following PACs having coupling intervals greater than the duration of the first time intervals.

4. A pacemaker according to claim 3 wherein the adjusting means increases the duration of the first time intervals responsive to tachyarrhythmias following a defined number of PACs having coupling intervals greater than the duration of the first time intervals.

5. A pacemaker according to claim 2 wherein the adjusting means decreases the duration of the first time intervals responsive to tachyarrhythmias following PACs having coupling intervals less than the duration of the first time intervals.

6. A pacemaker according to claim 5 wherein the adjusting means decreases the duration of the first time intervals responsive to tachyarrhythmias following a defined number of PACs having coupling intervals less than the duration of the first time intervals.

7. A pacemaker according to claim 2 wherein the adjusting means comprises a stored histogram having multiple interval range bins containing counts of PACs preceding detected tachyarrhythmias and having coupling intervals falling within corresponding interval ranges and wherein the adjusting means adjusts the duration of the first time intervals responsive to one of the bins having a count exceeding a defined threshold.

8. A pacemaker, comprising;
first and second atrial electrodes;
an atrial sense amplifier responsive to atrial depolarizations and coupled to the first atrial electrode;
an atrial pacing pulse generator coupled to the second atrial electrode;
control circuitry coupled to the atrial sense amplifier and to the pulse generator, defining first time intervals extending for a defined duration following atrial pacing pulses and triggering generation of pacing pulses by the pulse generator synchronized only to atrial depolarizations sensed by the atrial sense amplifier outside the first time intervals, the control circuitry further comprising an atrial tachyarrhythmia detector and means for adjusting the duration of the first time intervals responsive to detections of atrial tachyarrhythmias.

9. A pacemaker according to claim 8, wherein the adjusting means comprises means responsive to the atrial sense amplifier for identifying occurrences of Premature Atrial Contractions (PACs) and for measuring coupling intervals separating them from preceding atrial pacing pulses.

10. A pacemaker according to claim 9 wherein the adjusting means increases the duration of the first time intervals responsive to tachyarrhythmias following PACs having coupling intervals greater than the duration of the first time intervals.

11. A pacemaker according to claim 9 wherein the adjusting means decreases the duration of the first time intervals responsive to tachyarrhythmias following PACs having coupling intervals less than the duration of the first time intervals.

12. A pacemaker according to claim 9 wherein the adjusting means comprises a stored histogram having multiple interval range bins containing counts of PACs preceding detected tachyarrhythmias and having coupling intervals falling within corresponding interval ranges and wherein the adjusting means adjusts the duration of the first time intervals responsive to one of the bins having a count exceeding a defined threshold.

* * * * *

UNITED STATES PATENT AND TRADEMARK OFFICE
CERTIFICATE OF CORRECTION

PATENT NO.       : 7,590,448 B2   Page 1 of 1
APPLICATION NO.  : 11/380246
DATED            : September 15, 2009
INVENTOR(S)      : Bernhard de Vries It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 593 days.

Signed and Sealed this

Twenty-first Day of September, 2010

David J. Kappos
*Director of the United States Patent and Trademark Office*